United States Patent [19]

Farona et al.

[11] Patent Number: 4,877,917

[45] Date of Patent: Oct. 31, 1989

[54] METHOD OF POLYMERIZING α,ω-DIYNES

[75] Inventors: Michael F. Farona, Cuyahoga Falls; Ramji Srinivasan, Akron, both of Ohio

[73] Assignee: University of Akron, Akron, Ohio

[21] Appl. No.: 258,791

[22] Filed: Oct. 17, 1988

[51] Int. Cl.$^4$ ............................................. C07C 12/02
[52] U.S. Cl. ...................................... 585/416; 585/27
[58] Field of Search ......................................... 585/416

[56] References Cited

U.S. PATENT DOCUMENTS 2,990,434  6/1961  Smith .................................. 585/416

FOREIGN PATENT DOCUMENTS

55/94323  8/1979  Japan .

OTHER PUBLICATIONS

Accounts of Chemical Research, vol. 10, #1, Jan. 1977, pp. 1-8; "Transition-Metal-Catalyzed Acetylene Cyclizations in Organic Synthesis".

*Primary Examiner*—Curtis R. Davis
*Attorney, Agent, or Firm*—Oldham & Oldham Co.

[57] ABSTRACT

A method of cyclization of α,ω-diynes with a transition metal catalyst such as niobium or tantalum salts such as halogen to yield products such as dimers trimers and higher polymers which may have benzo cyclobutene groups, benzocyclopentene groups, benzocyclohexene groups, or none of these, depending on the size of n in the α,ω-diynes of the formula of page 1.

16 Claims, No Drawings

METHOD OF POLYMERIZING α,ω-DIYNES

FIELD OF THE INVENTION

This invention relates to a catalyst and aryl cyclobutene terminated alkane or a bis(aryl cyclobutene) alkane. More particularly, this invention relates to a niobium catalyst that yields bis(arylcyclobutene) terminated alkanes or products of cyclotrimerization of the acetylene groups to form substituted benzene groups. Specifically, this invention relates to a one step method for polymerizing 1,5-hexadiyne and related α, ω-diynes of usually up to about 12 carbon atoms in relatively high yields, usually 70 percent and higher than 80 percent to essentially 90 plus percent yield. The α,ω-diynes useful in this invention may be represented by formula $$HC \equiv C(CH_2)_n C \equiv C-H$$

where the tribond is represented as ≡ and n has preferably an even value such as 2, 4, 6, 8, 10, 12, etc.

PRIOR ART

The polyarylcyclobutenes also preferably designated as "polybenzocyclobutenes" are desirable compositions due to their high heat stability and chemical resistance. Consequently, they have been suggested for coatings, fibers and films and other uses. In general, these polyarylcyclobutenes are relatively expensive and their cost limits their usage. Also, their manufacture requires a number of chemical operations.

SUMMARY OF THE INVENTION AND ITS BEST MODES

The α,ω-diynes are available and we have discovered how to polymerize the α,ω-diynes of about 6 to 12 or more carbon atom to produce dimers, trimers and higher polymers relatively simply by use of a very cheap catalyst and ones that are readily available with little preparation cost.

The catalysts useful in this invention are the salts of the transition metals of the Periodic Table such as niobium or tantalum. The halogen salts of these metals are well suited for this purpose. Specific examples of useful catalysts are niobium chloride, niobium bromide, tantalum chloride and tantalum bromide. The catalyst where the nobium and tantalum are in the pentavalent states are the desirable ones. For instance, niobium pentachloride and tantalum pentachloride generally give more desirable results and are preferred over niobium bromide or tantalum bromide. The iodides are more expensive and the fluorides are dangerous and less desirable than the bromides and the chlorides.

The niobium and tantalum salts, such as the halides preferably of chloride and bromide may be used effectively with co-catalysts of tin. For example, the tin salts of the halogens may be used and the tin iodide salt of tetravalent tin are preferred. Also, the tetra organo tin compounds, such as the tetraaryl tins of phenyl, tolyl and related compounds may be used as co-catalysts. These co-catalysts may enhance polymer yield as shown by TABLE II and III.

The ratio of monomers to catalyst can affect the polymer yield, usually about 1 to 50-100 gives the better results, although ratios as high as 1 to 500 have been used.

The catalyst may be used without a solvent. The hydrocarbons can be used as a solvent. The catalysts are not as soluble in aliphatic hydrocarbons as they are in aromatic and cycloaliphatic hydrocarbons.

The α,ω-diynes useful in this invention contain acetylene groups located in the α and ω positions on the hydrocarbon. Usually they contain from about 6 to about 14 carbon atoms with those having 6 to 12 carbon atoms being preferred. Representative examples are 1,5-hexadiyne, 1,6-heptadiyne, 1,7-octadiyne, 1,9-decadiyne and 1,11-dodecadiyne.

We have discovered that our catalyst can dimerize, trimerize and produce polymers from the α, ω-diynes in relatively high yields at temperatures of ambient to 80° C. preferably in a solution of a suitable solvent. Suitable solvents are benzene, toluene, xylene and related liquid hydrocarbons, such as cyclohexane and halo carbons such as carbon tetrachloride or methylene dichloride.

The polymerization product can be recovered or freed from unreacted α,ω-diyne by treatment with an alcohol such as methanol and separating the phases. The solid precipitated phase is removed by filtration and the solvent in the filtrate is removed under vacuum. The residue from the solvent removal can be recrystallized from diethyl ether or hexanes to obtain a relatively pure product.

The nature of this invention and its advantages may be understood more readily by reference to the following representative and exemplary examples where all parts and percentages are by weight unless otherwise indicated.

EXAMPLE 1

A reaction flask was charged with 25 ml of benzene and $5.6 \times 10^{-4}$ moles of niobium chloride and 0.03 moles of 1,5-hexadiyne and allowed to react with stirring at room temperature. The solution turned dark brown; and, after 5 hours, the mixture was poured into methanol and 0.1 gram of black residue was obtained by filtration. The solvent in the filtrate was removed by vacuum distillation to leave a crude product. This product was recrystallized first in hexane and then in ether to give 1,2-bis(benzocyclobutenyl)ethane in 70.8 percent yield and a conversion of about 80 to 85 percent.

EXAMPLE 2

This example uses a mixture of $NbCl_5/SnPh_4$ as the catalyst to trimerize 1,5-hexadiyne (1.5 ml) in benzene (15 ml) with niobium chloride (75 mg) and tetraphenyltin (115 mg). The reaction was run for 5 hours at room temperature and terminated by addition of 1 ml of methanol. After 2 hours the mixture was filtered to remove the insoluble precipitate formed by the methanol treatment. The solvent in the filtrate was removed in a rotovac distillation apparatus. The residue from the distillation was dissolved in hexane (75 ml) and boiled with animal charcoal. Then it was filtered through a pad of celite. The celite was washed with hot hexane (20 ml) and the washing added to the filtrate. Hexane was removed under reduced pressure to obtain the purified 1,2-bis(benzocyclobutenyl) ethane in a yield of 85.5 percent.

When the same reaction was run in toluene (same conditions) the yield of 1,2-bis(benzocyclobutenyl)ethane was 90.0 percent. Thus, toluene is a preferred solvent.

Molecular weight determination of the polymers was done by GPC with polystyrene as the standard and using the Chromatix molecular weight program. DSC and TGA were performed using DuPont 1090 instrument.

EXAMPLE 3

Polymerization of 1,9-decadiyne Using NbCl$_5$ as a Catalyst in Toluene

Polymerization was carried out in a 2-neck, 250 ml flask fitted with a rubber septum and a gas adapter. The catalyst NbCl$_5$ 0.075 g, ($2.7 \times 10^{-4}$ moles) was weighed into the flask inside a glove bag to give an inert atmosphere. The gas adapter was then replaced by a condenser. Freshly distilled benzene (25 ml) was injected into the flask. The flask was then washed to 55° C. The monomer 1,9 decadiyne 2.0 g (0.014 moles) was added in drops. The reaction was exothermic and the color changed instantly from deep red to black. The run was stirred for 5 hours, after which 3 ml of methanol was added to quench the reaction. The mixture was then poured into 200 ml of methanol and stirred for 2 hours. The precipitate was filtered and was vacuum dried over 24 hours. Total weight of the polymer was 1.90 g (95 percent conversion) of which 85 percent was soluble in toluene.

EXAMPLE 4A

Polymerization of 1,7 Octadiyne using NbCl$_5$ as Catalyst and Tin Tetraphenyl as Co-catalyst

To a stirred solution of 1:1 mixture of NbCl$_5$ (0.150 g, $5.5 \times 10^{-4}$ moles) and tin tetraphenyl (0.237 g, $5.5 \times 10^{-4}$ moles) in toluene at 80° C. was added the monomer, 1,7-octadiyne. The color changed from dark red to black. The mixture was stirred for 5 hours and poured into 200 ml of methanol. A viscous polymer fluid precipitated that stuck to the walls of the beaker. After decanting the liquid, the polymer was dissolved in toluene, re-precipitated with methanol and the precipitate was dried under vacuum. The yield of polymer was 3.04 g (63 percent). The methanol soluble fraction (33 percent) was identified as 1,4-bis(benzocyclohexenyl)-butane.

EXAMPLE 4B

Polymerization of 1,11-dodecadiyne using NbCl$_5$ as catalyst

The reaction was carried out in the same manner as for 1,9 decadiyne. To a stirred solution of NbCl$_5$, 0.110 g, ($4.0 \times 10^{-4}$ mole) and tin tetraphenyl (0.170 g) in toluene 30 ml at 65° C. was added 1,11-dodecadiyne 3.2 g (0.019 mole) in drops. The reaction mixture was stirred and the product compared to the fluid product obtained in polymerization of 1,9-decadiyne. After 12 hours, the reaction mixture was poured into methanol and stirred for 2 hours to precipitate the polymer. It was removed by filtering and the filtrate was dried under vacuum for 24 hours. The weight of the polymer obtained was 3.16 g (or 98 percent). 95 percent of this polymer was soluble in toluene.

EXAMPLE 5

A number of experimental runs were made to polymerize 1,5-hexadiyne with different catalysts in different solvents. The runs were made at temperatures indicated and the polymer was recovered in accordance with the procedure of the examples. The monomer to catalyst ratio was 50. The specific catalyst, solvent, temperature, percent conversion and percent trimer produced by each run is shown in the following TABLES I–VI.

TABLE I

Cyclotrimerization of 1,5-Hexadiyne with Different Catalysts in Different Solvents

| Catalyst | Solvent | Temp °C. | % Conversion | % Trimer Yield |
| --- | --- | --- | --- | --- |
| NbCl$_5$ | Benzene | 55 | 85 | 70.8 |
| NbCl$_5$ | Toluene | 75 | 82–85 | 70.8 |
| NbCl$_5$/Cocat* | Benzene | 30 | 100 | 85.8 |
| NbCl$_5$/Cocat* | Toluene | 35 | 100 | 90.0 |
| TaCl$_5$ | Benzene | 55 | 70 | 58.0 |
|  | Toluene | 75 | 62 | 53 |
| NbBr$_5$/CoCat | Toluene | 80 | 95 | 35 |

Monomer to Catalyst = 50:1
Cocatalyst-Sn(C$_6$H$_5$)$_4$, (1:1)

TABLE II

Cyclotrimerization of 1,7-octadiyne (n-4) and 1,6-heptadiyne (n-3)

| Monomer | Catalyst | Solvent | Temp °C. | % Conversion | % Trimer | % Polymer |
| --- | --- | --- | --- | --- | --- | --- |
| 1,7-octadiyne | NbCl$_5$ | Benzene | 55 | 88 | 33 | 50 |
|  |  | Toluene | 80 | 90–95 | 38 | 53 |
|  | NbCl$_5$/Cocat* | Toluene | 80 | 100 | 33 | 63 |
|  | TaCl$_5$ | Toluene | 80 | 60 | 20 | 33 |
| 1,6 Heptadiyne | NbCl$_5$ | Toluene | 80 | 40 | 15 | 25 Insol. |
|  | TaCl$_5$ | Toluene | 80 | 35 | 15 | 20 Insol. |

Monomer/catalyst-50:1 *Cocatalyst-Sn(C$_6$H$_5$)$_4$; Catalyst:Cocatalyst-1:1 Temperature = 35° C.

TABLE III

Effect of Catalyst Concentration on the Cyclotrimerization of 1,5-Hexadiyne by NbCl$_5$

| | % Yield of Trimer | |
| Monomer:Catalyst | Without Cocatalyst | With Cocatalyst |
| --- | --- | --- |
| 50:1 | 70.8 | 99.3 |
| 100:1 | 65.3 | 90.1 |
| 200:1 | 57.6 | 81.0 |
| 500:1 | 33.0 | 68.3 |

Cocatalyst - (C$_6$H$_5$)$_4$Sn
Solvent - Toluene
Temperature = 55° C.

TABLE IV

Effects of Various Cocatalysts on the Cyclotrimerization of 1,5-Hexadiyne by NbCl$_5$

| Cocatalyst | % Conversion | % Trimer |
| --- | --- | --- |
| (C$_6$H$_5$)$_4$Sn | 100 | 90.1 |
| (n-Bu)$_4$Sn | 100 | 91.4 |
| (CH$_3$)$_3$SnCl | 100 | 91.1 |
| (n-Bu)$_3$SnCl | 96 | 88.4 |
| SnI$_4$ | 92 | 82.5 |
| EtAlC$_2$ | 88 | 65.0 |

CoCatalyst to Catalyst Ratio-1:1
Solvent-Toluene
Temperature = 35° C.

TABLE V

Reaction of 1,5-Hexadiyne and Trimethylsilylacetylene at Different Monomer Ratios

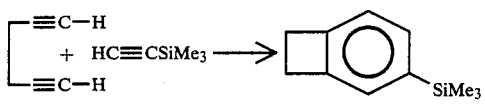

| Monomer Ratios | | Catalyst | % Conversion | Yield % |
|---|---|---|---|---|
| 1,5-HD | TMSA | | | |
| 1 | 1 | NbCl$_5$ | 85 | 52 |
| 1 | 2 | NbCl$_5$ | 85 | 52 |
| 1 | 5 | NbCl$_5$ | 78 | 53 |
| 2 | 1 | NbCl$_5$ | 88 | 59 |
| 1 | 1 | NbCl$_5$/Cocat* | 90 | 33 |
| 5 | 1 | NbCl$_5$ | 100 | 59 |

*Cocatalyst = Sn(C$_6$H$_5$)$_4$
Solvent = toluene and a temperature of 25° C.

TABLE VI

Cyclization:-1,5-hexadiyne with other 1-alkynes by NbCl$_5$

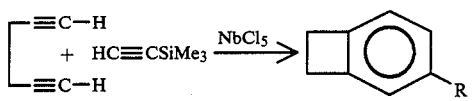

| R | Solvent | Temp °C. | Conversion | Yield |
|---|---|---|---|---|
| SiMe$_3$ | Toluene | 25 | 80 | 52 |
| —(CH$_2$)$_3$Cl | Toluene | 80 | 100 | 38 |
| —C$_6$H$_5$ | Toluene | 80 | 80 | 18 |

R may be also trialkyl Si with the alkyl having 1 to about 10 carbon atoms and other alkyl substituted aryl radicals
R may also be vinyl or substituted vinyl, —CH$_2$Cl, and related groups

EXAMPLE 6

This example provides a method for producing aryl cyclobutene derivatives that have great value as starting material in preparing specific arylcyclobutenes which may be used in a conventional way or to yield polymers with reactive groups. Particularly desirable as a derivative is the trialkyl silyl derivative as it can be readily converted to other derivatives having a specific group in a predetermined position.

Equal molar amounts of the α,ω-diyne, for instance 1,5-hexadiyne and trimethylsilylacetylene are charged to a reactor and the catalyst, such as those of TABLE V and VI is added and the reactin is allowed to occur and the reaction mixture worked up by methanol treatment following the treatment of the examples.

TABLE V shows that the tetraphenyl tin co-catalyst materially reduces the yield of the aryl cyclobutene trimethyl silyl derivative relative to the yield where the catalyst does not contain the co-catalyst.

Table VII shows the preparation details of the polymerization run on 1,7-octadiyne (1,7-OD), 1,9-decadiyne (1,9-OD), and 1,11-dodecadiyne (1,11-DDD). Some comments on the results of the polymerization are appropriate. In the case of 1,7-octadiyne, Table VII reports only that portion of the polymer that is soluble in toluene; the remainder of the products, to account for the high conversion, was 1,4-bis(benzocyclohexenyl)butane. In the case of TaCl$_5$ as the catalyst, high conversions to polymers were obtained, but the products were gels and mostly insoluble. For the NbCl$_5$ or NBCl$_5$/Sn(C$_6$H$_5$)$_4$ catalysts, high conversions were obtained and the polymers contained little gel.

TABLE VII

Polymerization of HC≡C(CH$_2$)$_n$C≡CH

| Monomer | Catalyst | Solvent | T, C°. | Conversion % | Polymer* % |
|---|---|---|---|---|---|
| n = 4 | a | Bz | 55 | 88 | 55 |
| | a | Tol | 80 | 90–95 | 53 |
| | b | Tol | 80 | 100 | 63 |
| | c | Tol | 80 | 60 | 33 |
| n = 6 | a | Tol | 65 | 100 | 80 |
| | a | Bz | 55 | 95 | 85 |
| | b | Tol | 65 | 100 | 95 |
| | c | Tol | 65 | 100 | 20 |
| | c | Bz | 55 | 100 | 5 |
| n = 8 | a | Bz | 55 | 95 | 80 |
| | a | Tol | 65 | 90 | 85 |
| | b | Tol | 65 | 100 | 95 |
| | c | Bz | 55 | 100 | 0 |
| | | Tol | 65 | 100 | 5 |

*% of polymer soluble in toluene; a = NbCl$_5$; b = NbCl$_5$/SN(C$_6$H$_5$)$_4$; c = TaCl$_5$; Monomer: MCl$_5$ = 50:1; where M is bNb or Ta; Bz = benzene; Tol = toluene The product from the polymerization of 1,4-diethynylbenzene was totally insoluble in common organic solvents. This polymer was studied by DSC and 13$_C$ solid state) measurements.

While in accordance with the patent statutes only the best mode and preferred embodiment of the invention has been illustrated and described in detail, it is to be understood that the invention is not limited thereto or thereby, but that the scope of the invention is defined by the appended claims.

What is claimed is:

1. A method of reacting an α,ω-diyne to form products containing at least one of the class of dimers, timers and higher polymers comprising contacting said α,ω-diyne either as a sole reactant or together with an alkyne with a niobium catalyst or tantalum catalyst to effect formation of a benzo product characterized as highly soluble to insoluble in benzene at 25° C.

2. The method of claim 1 where the niobium catalyst is selected from the class of niobium halide and niobium halide reacted with tin aryl or alkyl or cycloalkyl compounds and the temperature of reaction is about ambient to 80° C.

3. The method of claim 1 where the reaction was terminated by addition of a terminating agent to form a precipitate, removing the precipitate and washing and reprecipitating said precipitate from a solvent to give a product free of α,ω-diyne.

4. The method of claim 1 wherein the α,ω-diyne is 1,5-hexadiyne.

5. The method of claim 1 wherein the product is 1,2-bis(benzocyclobutenyl)ethane.

6. The method of claim 1 wherein the α,ω-diyne contains from 6 to about 14 carbon atoms.

7. The method of claim 1 wherein the polymer contains a terminal aryl cyclobutene group connected to an alkyl radical having at least 2 carbon atoms.

8. The method of claim 1 wherein the polymerization occurs in the presence or an aromatic solvent selected from the class consisting of benzene, toluene, and ethylbenzene.

9. A method of reacting an α,ω-diyne of the formula H—C≡C(CH$_2$)$_n$C≡CH where n is an integer 2 and higher to form a product containing at least one of the species of the class consisting of dimer, trimer or higher polymer comprising contacting said α,ω-diyne with a catalyst comprising a tantalum catalyst or a niobium catalyst, or salts of said catalyst or co-catalyst of said salts with tin salts or organic tin compound at a temperature of about 10° to boiling point of the α,ω-diyne.

10. The method of claim 9 wherein the product contains a high percentage of polymers other than trimers.

11. The method of claim 10 wherein the polymer contains little gel and is essentially soluble in toluene at 25° C.

12. The method of claim 9 wherein tantalium and niobium are present as salts of the halogens chlorine and bromine and the co-catalyst is a halide of tin or a tetra aryl tin.

13. The method of claim 9 wherein at least part of the α,ω-diyne reacts with trialkyl silylacetylene to yield a product having at least one trialkyl silyl group.

14. The method of claim 9 wherein at least part of α,ω-diyne polymerizes with an acetylene having the formula H—C≡CR and R is hydrogen, trialkyl Si alkyl halide, and tri-alkyl aryl-radicals.

15. The method of claim 9 wherein R is trimethyl Si radical.

16. The method of claim 9 wherein the polymerization occurs in the presence of an aromatic solvent selected from the class consisting of benzene, toluene and ethylbenzene.

* * * * *